(12) United States Patent
Hu

(10) Patent No.: US 11,350,962 B2
(45) Date of Patent: Jun. 7, 2022

(54) FLEXIBLE MEDICAL SCISSORS

(71) Applicant: THE FIRST HOSPITAL AFFILIATED TO ARMY MEDICAL UNIV, Chongqing (CN)

(72) Inventor: Rong Hu, Chongqing (CN)

(73) Assignee: THE FIRST HOSPITAL AFFILIATED TO ARMY MEDICAL UNIV, Chongqing (CN)

(*) Notice: Subject to any disclaimer, the term of this patent is extended or adjusted under 35 U.S.C. 154(b) by 0 days.

(21) Appl. No.: 17/506,712

(22) Filed: Oct. 21, 2021

(65) Prior Publication Data

US 2022/0039823 A1 Feb. 10, 2022

Related U.S. Application Data

(63) Continuation of application No. PCT/CN2020/085856, filed on Apr. 21, 2020.

(30) Foreign Application Priority Data

Jun. 13, 2019 (CN) .......................... 201910512762.2

(51) Int. Cl.
*A61B 17/3201* (2006.01)
*A61B 17/32* (2006.01)
*A61B 17/00* (2006.01)

(52) U.S. Cl.
CPC .. *A61B 17/3201* (2013.01); *A61B 17/320016* (2013.01); *A61B 2017/00292* (2013.01)

(58) Field of Classification Search
CPC ................... A61B 17/320016; A61B 17/3201
See application file for complete search history.

(56) References Cited

U.S. PATENT DOCUMENTS

| 5,904,702 A | 5/1999 | Ek et al. |
| 8,721,657 B2 | 5/2014 | Kondoh et al. |
| 2010/0198244 A1 | 8/2010 | Spivey et al. |
| 2019/0021752 A1* | 1/2019 | Boudreaux ........ A61B 17/2202 |

FOREIGN PATENT DOCUMENTS

| CN | 102573672 A | 7/2012 |
| CN | 208573795 U | 3/2019 |
| CN | 110123419 A | 8/2019 |
| CN | 2210301145 U | 4/2020 |

OTHER PUBLICATIONS

International Search Report issued in corresponding International application No. PCT/CN2020/085856, dated Jun. 11, 2020.
Written Opinion of the International Search Authority in corresponding International application No. PCT/CN2020/085856.

* cited by examiner

*Primary Examiner* — Sarah A Simpson

(57) ABSTRACT

The present disclosure provides flexible medical scissors, including a main body, a lifting mechanism, an adjusting mechanism, a flexible sleeve, and a shearing mechanism. The flexible medical scissors provide the lifting mechanism at a top of a handle, the finger sleeve in the lifting mechanism sleeves a ring finger of a user, when using, the finger sleeve is pulled to enable the pull rope to pull the rotating shaft, and the rotating shaft drives the movable cutter to rotate, so that a shearing function is realized. The adjusting mechanism is disposed at a bottom of the handle, three groups of sliding grooves are formed in the adjusting mechanism, and sliding columns are respectively disposed in the sliding grooves.

9 Claims, 4 Drawing Sheets

FLEXIBLE MEDICAL SCISSORS

TECHNICAL FIELD

The present disclosure relates to a related field of medical instruments, and in particular to flexible medical scissors.

BACKGROUND

Surgery refers to a treatment of cutting, suturing, and the like on a body of a patient by a medical instrument, and an operation performed on a local part of a human body using instruments like scissors, needles, etc., maintains health of the patient, which is a main treatment method of the surgery department and is commonly referred to "operate". The surgery aims to cure or diagnose a disease, such as removing disease tissue, repairing damage, transplanting organs, improving function and morphology of organisms, etc. During the surgery, it is necessary to use scissors. When lesions in the human body need to be removed, a risk of operation is increased due to a fact that some parts have important vascular nerves, resulting in a poor surgical effect.

SUMMARY

In order to solve the above disadvantages, the present disclosure provides flexible medical scissors.

The present disclosure provides the flexible medical scissors, including a main body, a handle, a lifting mechanism, adjusting mechanisms, a flexible sleeve, a first fixing disc, an elastic pipe, a second fixing disc, a shearing mechanism, a movable cutter, a fixed cutter, a rotating shaft, a winding column, a fixing cylinder, a circular groove, a square groove, a connecting wire, a clamping block, an adjusting disc, a spring, a telescopic pull wire, a telescopic adjusting cylinder, an adjusting groove, fixing grooves, a connecting block, an annular groove, and a movable ball. The handle is disposed at an upper end of the main body, the lifting mechanism is disposed at a top of the handle, three groups of the adjusting mechanisms are disposed at a bottom three centimeters position of the handle, the flexible sleeve is disposed and sleeved with a bottom of the adjusting mechanisms, the first fixing disc is fixedly disposed at a bottom of the flexible sleeve, the elastic pipe is tightly attached to a bottom of the first fixing disc, the second fixing disc is fixedly disposed at a bottom of the elastic pipe, and the shearing mechanism is disposed at a bottom of the second fixing disc. The movable cutter is disposed at an upper end in the shearing mechanism, the fixed cutter is disposed at a lower end of the movable cutter, an upper end in the fixed cutter is rotated with the movable cutter through the rotating shaft, and an upper end in the movable cutter is welded with the rotating shaft, a top of the rotating shaft is embedded with a winding column. The fixing cylinder is disposed at a bottom of the handle, the circular groove is disposed at an upper end in the fixing cylinder, the square groove is disposed at a bottom of the circular groove, the telescopic pull wire extends from the circular groove, a tail end of the telescopic pull wire is embedded in the clamping block, and the clamping block is matched with the square groove. The adjusting disc is vertically disposed at a lower end in the shearing mechanism, the spring is welded in a middle of a top end of the second fixing disc, the telescopic pull wire is fixed in a middle through hole in the second fixing disc, the telescopic adjusting cylinder is disposed at a rear surface of the adjusting mechanism, the adjusting groove is formed in a middle of the telescopic adjusting cylinder, four groups of the fixing grooves are uniformly distributed at a right end of the adjusting groove, the connecting block is inserted at a bottom of the adjusting groove, a bottom of the connecting block is fixed to the telescopic pull wire, the annular groove is formed at a position in the adjusting disc where the position is 0.5 centimeters from an edge of the adjusting disc, the movable ball is movably disposed in the annular groove, and a middle of a top end of the movable ball is fixed with the connecting wire. The lifting mechanism includes a finger sleeve, a rubber rope, and a pull rope. The finger sleeve is in a circular shape, and a left side of the finger sleeve is in hot melting connection with the rubber rope. The pull rope is embedded at a bottom of the rubber rope, and a bottom three centimeters portion of the pull rope is wound around an outer diameter surface of the winding column.

The flexible medical scissors provide the lifting mechanism at the top of the handle, the finger sleeve in the lifting mechanism sleeves a ring finger of a user, when using, the finger sleeve is pulled to enable the pull rope to pull the rotating shaft, and the rotating shaft drives the movable cutter to rotate, so that a shearing function is realized. The adjusting mechanism is disposed at the bottom of the handle, three groups of sliding grooves are formed in the adjusting mechanism, and sliding columns are respectively disposed in the sliding grooves. When the sliding columns are slid to different positions in the sliding grooves to fix, the pull wires are configured to pull, so that two groups of connecting plates have different connection angles, and the flexible sleeve may be bent at different angles. The spring in the shearing mechanism is controlled by the telescopic pull wire to control a length of the shearing mechanism, so that a surgical channel may conveniently enter a patient body. In addition, the adjusting disc is disposed at the upper end of the shearing mechanism, after the user pulls the connecting wire according to an angle, the shearing mechanism is adjusted in multiple angles and in all directions, so that important blood vessels and nerves may be bypassed according to natural gaps of human body tissues and lesions are reached in a roundabout way for surgery operation.

DETAILED DESCRIPTION

Figure 1:
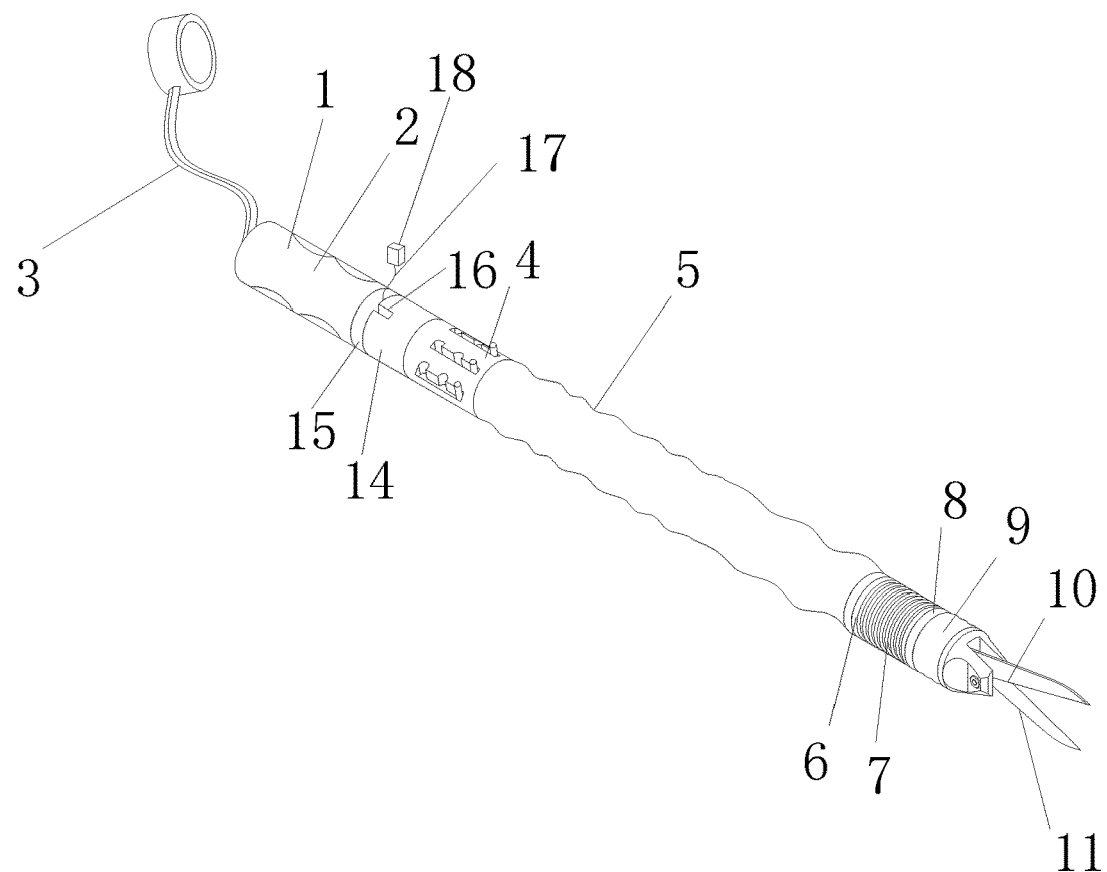
FIG. 1 is a structural schematic diagram of the present disclosure.
Figure 2:
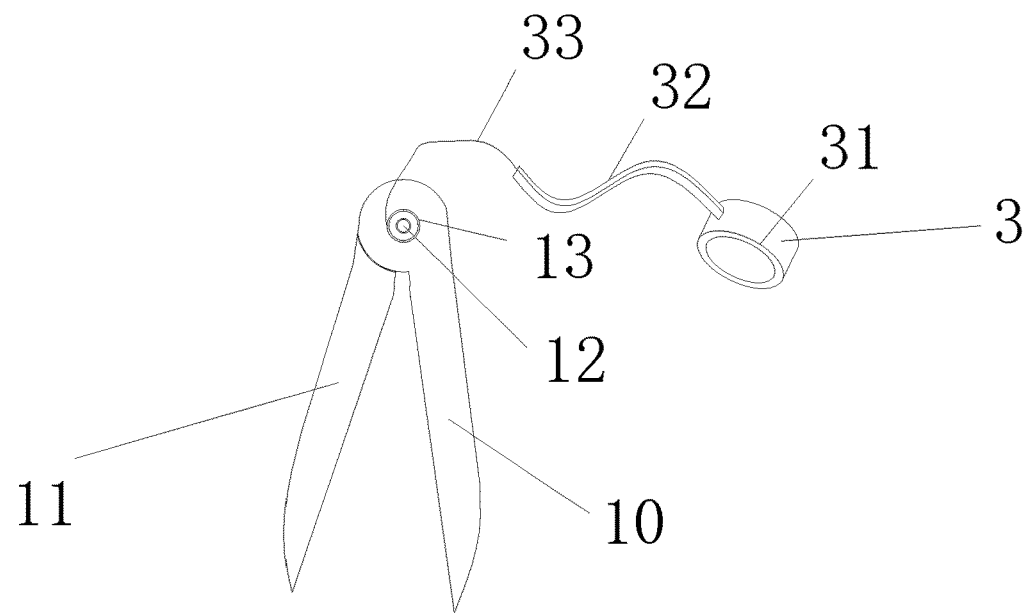
FIG. 2 is a structural schematic diagram of a lifting mechanism of the present disclosure.
Figure 3:
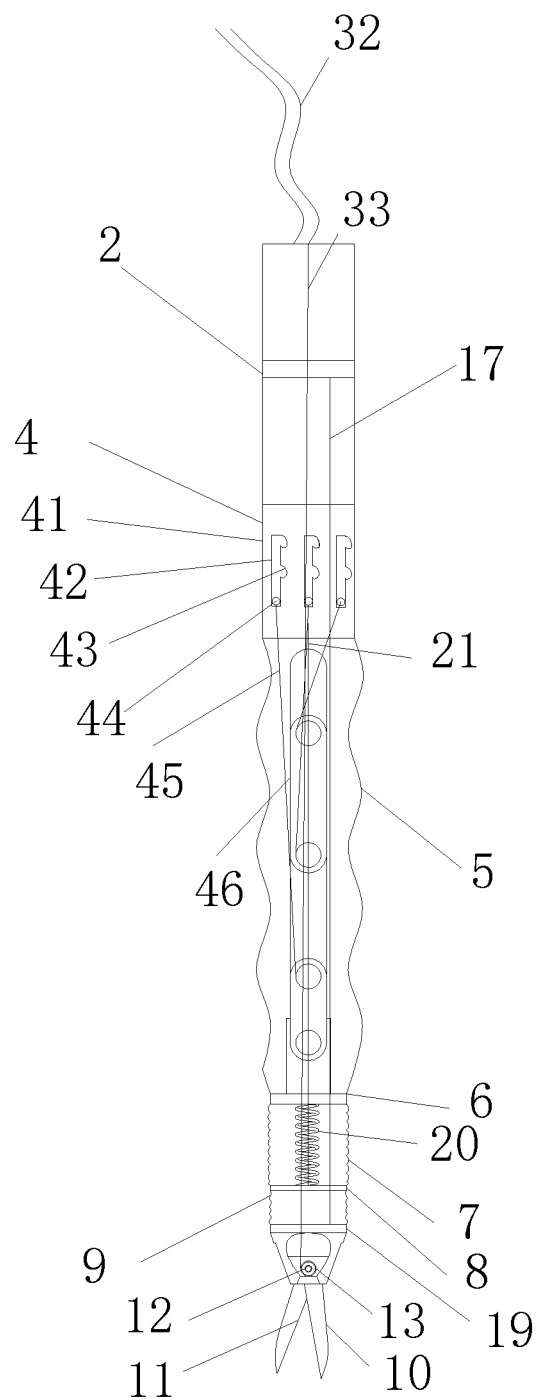
FIG. 3 is an inner structural schematic diagram of a main body of the present disclosure.
Figure 4:
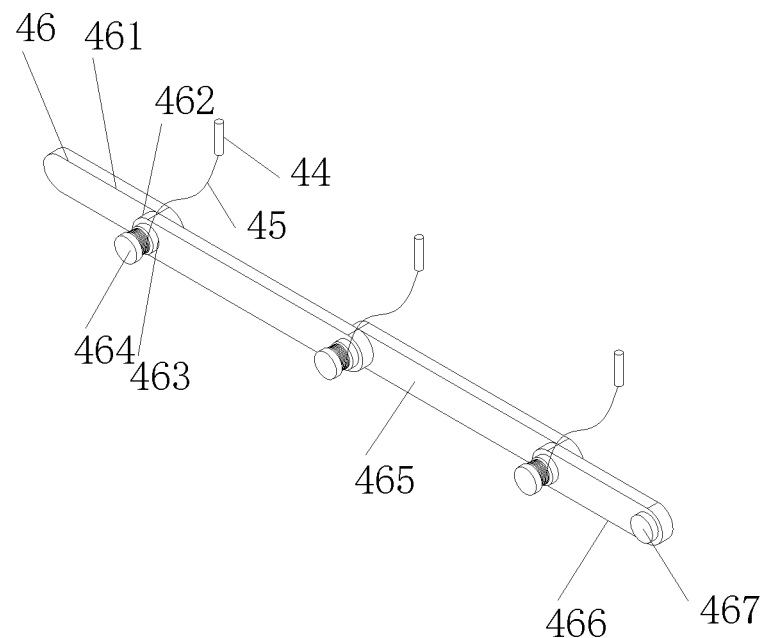
FIG. 4 is a structural schematic diagram of one of adjusting plates of the present disclosure.
Figure 5:
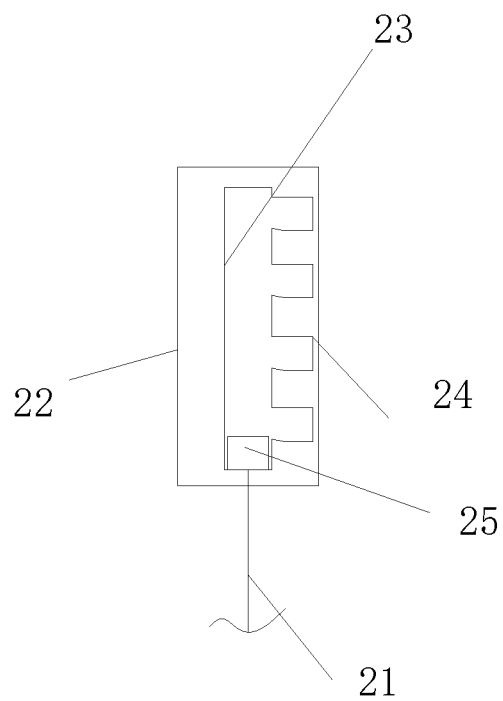
FIG. 5 is a structural schematic diagram of a telescopic adjusting cylinder of the present disclosure.
Figure 6:
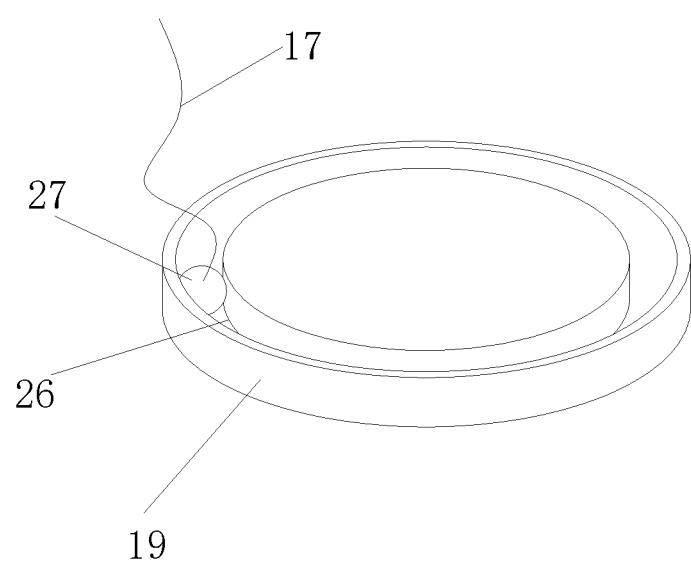
FIG. 6 is a structural schematic diagram of an adjusting disc of the present disclosure.

The present disclosure is described in details below in conjunction with FIGS. 1-6 to provide a clear and complete description of technical solutions in embodiments of the present disclosure. Obviously, the described embodiments are merely some embodiments of the present disclosure, rather than all of the embodiments. All other embodiments obtained by those who skilled in the art based on the embodiments of the present disclosure without creative efforts shall fall within protection scopes of the present disclosure.

The present disclosure provides flexible medical scissors, including a main body 1, a handle 2, a lifting mechanism 3, adjusting mechanisms 4, a flexible sleeve 5, a first fixing disc 6, an elastic pipe 7, a second fixing disc 8, a shearing mechanism 9, a movable cutter 10, a fixed cutter 11, a rotating shaft 12, a winding column 13, a fixing cylinder 14, a circular groove 15, a square groove 16, a connecting wire 17, a clamping block 18, an adjusting disc 19, a spring 20, a telescopic pull wire 21, a telescopic adjusting cylinder 22, an adjusting groove 23, fixing grooves 24, a connecting block 25, an annular groove 26, and a movable ball 27. The handle 2 is disposed at an upper end of the main body 1, the lifting mechanism 3 is disposed at a top of the handle 2, three groups of the adjusting mechanisms 4 are disposed at a bottom three centimeters position of the handle 2, the flexible sleeve 5 is disposed and sleeved with a bottom of the adjusting mechanisms 4, the first fixing disc 6 is fixedly disposed at a bottom of the flexible sleeve 5, the elastic pipe 7 is tightly attached to a bottom of the first fixing disc 6, the second fixing disc 8 is fixedly disposed at a bottom of the elastic pipe 7, and the shearing mechanism 9 is disposed at a bottom of the second fixing disc 8. The movable cutter 10 is disposed at an upper end in the shearing mechanism 9, the fixed cutter 11 is disposed at a lower end of the movable cutter 10, an upper end in the fixed cutter 11 is rotated with the movable cutter 10 through the rotating shaft 12, and an upper end in the movable cutter 10 is welded with the rotating shaft 12, a top of the rotating shaft 12 is embedded with a winding column 13. The fixing cylinder 14 is disposed at a bottom of the handle 2, the circular groove 15 is disposed at an upper end in the fixing cylinder 14, the square groove 16 is disposed at a bottom of the circular groove 15, the telescopic pull wire 21 extends from the circular groove 15, a tail end of the telescopic pull wire 21 is embedded in the clamping block 18, and the clamping block 18 is matched with the square groove 16. The adjusting disc 19 is vertically disposed at a lower end in the shearing mechanism 9, the spring 20 is welded in a middle of a top end of the second fixing disc 8, the telescopic pull wire 21 is fixed in a middle through hole in the second fixing disc 8, the telescopic adjusting cylinder 22 is disposed at a rear surface of the adjusting mechanism 4, the adjusting groove 23 is formed in a middle of the telescopic adjusting cylinder 22, four groups of the fixing grooves 24 are uniformly distributed at a right end of the adjusting groove 23, the connecting block 25 is inserted at a bottom of the adjusting groove 23, a bottom of the connecting block 25 is fixed to the telescopic pull wire 21, the annular groove 26 is formed at a position in the adjusting disc where the position is 0.5 centimeters from an edge of the adjusting disc 19, the movable ball 27 is movably disposed in the annular groove 26 and a middle of a top end of the movable ball 27 is fixed with the connecting wire 17. The lifting mechanism 3 includes a finger sleeve 31, a rubber rope 32, and a pull rope 333. The finger sleeve 31 is in a circular shape, and a left side of the finger sleeve 31 is in hot melting connection with the rubber rope 32. The pull rope 33 is embedded at a bottom of the rubber rope 32, and a bottom three centimeters portion of the pull rope 33 is wound around an outer diameter surface of the winding column 13.

The adjusting mechanism 4 includes a clamping sleeve 41, sliding grooves 42, clamping grooves 43, sliding columns 44, and pull wires 45, and adjusting plates 46. A top of the clamping sleeve 41 is vertically welded to a bottom of the handle 2, a bottom of the clamping sleeve 41 is fixed to the flexible sleeve 5, three groups of the sliding grooves 42 having a depth of twelve millimeters are uniformly distributed in the clamping sleeve 41 along a left-to-right end, each of the clamping grooves having a semicircular shape is respectively formed in a middle right end and an upper end of each of the sliding grooves 42, each of the sliding columns 44 is disposed in each of the sliding grooves 42, and each of the sliding columns 44 is respectively and slidably connected with each of the sliding grooves 42. Each of the pull wires is respectively embedded at a bottom of each of the sliding columns 44, and a bottom of each of the pull wires 45 penetrates through a bottom of the clamping sleeve 41 and is respectively fixed with each of the adjusting plates 46, which is convenient for movement and further convenient to adjust angles between connecting plates.

Each of the adjusting plates 46 includes a fixing plate 461, a first connecting plate 462, rotation shafts 463, wire columns 464, a second connecting plate 465, and a rotating plate 466. A first of the rotation shafts 463 is embedded in a lower end in the fixing plate 461, and the first of the rotation shafts 463 rotates with a first end of the first connecting plate 462 on an outer diameter surface of the first of the rotation shafts 463, a first of the wire columns 464 is vertically fixed on a top of the first of the rotation shafts 463, and an outer diameter surface of the first of the wire columns 464 is fixedly wound with a respective one of the pull wires 45, a second end of the first connecting plate 462 is further rotated with a first end of the second connecting plate 465 through a second of the rotation shafts 463, and a second end of the second connecting plate 465 is rotated with the rotating plate 46 through a third of the rotation shafts 463. The movable shaft 467 is embedded in a lower end of the rotating plate 466, and the movable shaft 467 is fixed with an upper end in the first fixing disc 6 through a steel plate, which has a good adjustment effect and is convenient and rapid.

An inner diameter of the finger sleeve 31 is 1.2 centimeters, and an inner surface of the finger sleeve 31 is bonded with a layer of anti-skid silica gel layer, which prevents from slipping when snapping in.

Bottom five centimeters portions, of the pull rope 33 and the pull wires 45, are all elastic segments, and a maximum stretching length is eight centimeters, so that the pull rope 33 and a lower end of each of the pull wires may rebound after being pulled out.

An outer diameter of each of the sliding columns 44 is smaller than an inner diameter of each of the sliding grooves 42 and an inner diameter of each of the clamping grooves 43, and a lower end of the outer diameter surface of each of the sliding columns 44 is frosted, so that the sliding columns 44 is prevented from sliding out due to shaking.

Three groups of the wire columns 464 are disposed on each of the adjusting plates 46, and each lower end of the pull wires 45 is respectively fixed to the three groups of the wire columns 464 to achieve adjustment from different angles.

An upper three centimeters end of the connecting wire 17 is an elastic portion, and a bottom of the connecting wire 17 is a fixed portion, which is convenient to stretch and have a good effect.

An outer diameter of the movable ball 27 is smaller than a top width of the annular groove 26, so that the movable ball 27 is prevented from sliding out.

The flexible sleeve 5 is made of medical silicone rubber.

| Property | Material | Medical Silicone Rubber | Common Silica Gel |
|---|---|---|---|
| Hygiene | | Strong | Poor |
| Environmental Protection | | High | Low |

According to the above table, the flexible sleeve 5 of the present disclosure is made of medical silicone rubber, which may achieve effects of sanitation and environmental protection.

The shearing mechanism 9 is made of 304 stainless steel.

| Property | Material | 304 stainless steel | Cast Iron |
|---|---|---|---|
| Hygiene | | Strong | Poor |
| Color | | Good | Poor |

According to the above table, the shearing mechanism 9 of the present disclosure is made of the 304 stainless steel, which may achieve effects of sanitation and good color.

The first connecting plate 462 and the second connecting plate 465 are made of PP plastic.

| Property | Material | PP | PVC |
|---|---|---|---|
| Environmental Protection | | High | Low |
| Odor | | Odorless | Large Odor |

According to the above table, the first connecting plate 462 and the second connecting plate are made of PP plastic materials, which achieves effects of environmental protection and no odor.

The present disclosure provides the flexible medical scissors, and the flexible medical scissors are operated in following manner.

First, when the flexible medical scissors are to be used, the flexible medical scissors are first sterilized, then a user holds the handle 2, and puts a ring finger of the hand holding the handle 2 into the finger sleeve 31 in the lifting mechanism 3, and then operation is to begin.

Second, when it is necessary to operate the shearing mechanism 9, the inner ring finger have a backward dragging force, so that the finger sleeve 31 drives the rubber rope 32 to pull the pull rope 33 to pull the winding column 10 at the top of the rotating shaft 12, and then the winding column 10 rotates to drive the rotating shaft 12 at the bottom to drive the movable cutter 7 to move for a work, so that when the movable cutter 7 needs to be closed, only the finger sleeve 31 needs to be retracted, and since the lower end of the pull rope 33 is the elastic segment, the winding column 10 is retracted, and the rotating shaft 12 makes the movable cutter 7 fallback and close.

Third, when it is necessary to enter a penitent body for operation, the movable cutter 7 needs to be closed to enter the patient body, and then it is determined according to bending of blood vessels when it is necessary to bypass important blood vessels and nerves, the user slides the sliding columns 44 in the sliding grooves 42 using the ring finger, and the sliding columns 44 may pull the wire columns 464 of the rotation shafts 463 in the second connecting plates 465 through the pull wires 45 and bend the second connecting plates 465 through rotation of the rotation shaft 463. The clamping grooves 43 are disposed in the sliding grooves 42, and when the sliding columns 44 are fixed in the clamping grooves 43, an adjusted angle may be fixed. After the second connecting plates 465 are adjusted, the flexible sleeve 5 may be bent to achieve an effect of bypassing the important blood vessels and nerves. Retracting the sliding columns 44 may retract the second connecting plates 465. When it is necessary to adjust positions of the fixing plates 461 and the first connecting plates 462, according to the adjusting method of the second connecting plate 465, the sliding column 44 in the sliding groove 42 in the middle may adjust the positions of the first connecting plates 462, the sliding column 44 in the sliding groove 42 in the right may adjust the positions of the fixing plates 461, and the flexible sleeve 5 may be bent at different angles, so as to bypass the important blood vessels and nerves according to the natural gaps of the human body tissues and lesions are reached in a roundabout way for surgery operation.

Fourth, when the main body 1 needs to extend into a surgical channel to enter the human body, the user releases elastic force of the telescopic pull wire 21 through the connecting block 25, then falls into a bottom of the adjusting groove 23, and the spring 20 at the bottom may release the pushing force, so that the shearing mechanism 9 extends into the human body, when the main body needs to be retracted, the telescopic pull wire 21 is pulled back through the connecting block 25, so that the second fixing disc 8 compresses the spring 20, then the connecting block 25 is slid into the fixing groove 24, and adjustment of different lengths is achieved. After entering the human body, an angle of the shearing mechanism 9 needs to be adjusted to achieve an optimal shearing angle of the lesions, and then the user may pull the clamping block 18 to enable the connecting wire 17 to adjust the movable ball 27, and since the movable ball 27 slides in the annular groove 26 and may slide to the required angle, adjusting in multiple angles may be realized by pulling the movable ball 27.

The flexible medical scissors provide the lifting mechanism 3 at the top of the handle 2, the finger sleeve 31 in the lifting mechanism 3 sleeves the ring finger of the user, when using, the finger sleeve 31 is pulled to enable the pull rope 32 to pull the rotating shaft 12, and the rotating shaft 12 drives the movable cutter 10 to rotate, so that a shearing function is realized. The adjusting mechanism 4 is disposed at the bottom of the handle 2, the three groups of the sliding grooves 42 are formed in the adjusting mechanism 4, and sliding columns 44 are respectively disposed in the sliding grooves 42. When the sliding columns 44 are slid to different positions in the sliding grooves 42 to fix, the three groups of the rotation shafts 467 in the adjusting plates 46 are pulled through the pull wires 45, so that two groups of the connecting plates have different connection angles, and the flexible sleeve 5 may be bent at different angles. The spring 20 in the shearing mechanism 9 is controlled by the telescopic pull wire 21 to control a length of the shearing mechanism 9, so that the surgical channel may conveniently enter the patient body. In addition, the adjusting disc 19 is disposed at the upper end of the shearing mechanism 9, after the user pulls the connecting wire 17 according to an angle, the shearing mechanism 9 is adjusted in multiple angles and in all directions, so that the important blood vessels and nerves may be bypassed according to the natural gaps of the human body tissues and the lesions are reached in the roundabout way for the surgery operation.

What is claimed is:
1. Flexible medical scissors, comprising:
   a main body, a handle, a lifting mechanism, adjusting mechanisms, a flexible sleeve, a first fixing disc, an elastic pipe, a second fixing disc, a shearing mechanism, a movable cutter, a fixed cutter, a rotating shaft, a winding column, a fixing cylinder, a circular groove, a square groove, a connecting wire, a clamping block, an adjusting disc, a spring, a telescopic pull wire, a telescopic adjusting cylinder, an adjusting groove, fixing grooves, a connecting block, an annular groove, and a movable ball;

wherein the handle is disposed at an upper end of the main body, the lifting mechanism is disposed at a top of the handle, three groups of the adjusting mechanisms are disposed at a bottom three centimeters position of the handle, the flexible sleeve is disposed and sleeved with a bottom of the adjusting mechanisms, the first fixing disc is fixedly disposed at a bottom of the flexible sleeve, the elastic pipe is tightly attached to a bottom of the first fixing disc, the second fixing disc is fixedly disposed at a bottom of the elastic pipe, and the shearing mechanism is disposed at a bottom of the second fixing disc; the movable cutter is disposed at an upper end of the shearing mechanism, the fixed cutter is disposed at a lower end of the movable cutter, an upper end of the fixed cutter is rotated with the movable cutter through the rotating shaft, and an upper end of the movable cutter is welded with the rotating shaft, a top of the rotating shaft is embedded with the winding column; the fixing cylinder is disposed at a bottom of the handle, the circular groove is disposed at an upper end of the fixing cylinder, the square groove is disposed at a bottom of the circular groove, the telescopic pull wire extends from the circular groove, a tail end of the telescopic pull wire is embedded in the clamping block, and the clamping block is matched with the square groove; the adjusting disc is vertically disposed at a lower end in the shearing mechanism, the spring is welded in a middle of a top end of the second fixing disc, the telescopic pull wire is fixed in a middle through hole in the second fixing disc, the telescopic adjusting cylinder is disposed at a rear surface of the adjusting mechanisms, the adjusting groove is formed in a middle of the telescopic adjusting cylinder, four groups of the fixing grooves are uniformly distributed at a right end of the adjusting groove, the connecting block is inserted at a bottom of the adjusting groove, a bottom of the connecting block is fixed to the telescopic pull wire, the annular groove is formed at a position in the adjusting disc where the position is 0.5 centimeters from an edge of the adjusting disc, the movable ball is movably disposed in the annular groove, and a middle of a top end of the movable ball is fixed with the connecting wire; the lifting mechanism comprises a finger sleeve, a rubber rope, and a pull rope, wherein the finger sleeve is in a circular shape, and a left side of the finger sleeve is in hot melting connection with the rubber rope; the pull rope is embedded at a bottom of the rubber rope, and a bottom three centimeters portion of the pull rope is wound around an outer diameter surface of the winding column.

2. The flexible medical scissors according to claim 1, wherein the adjusting mechanisms comprise a clamping sleeve, sliding grooves, clamping grooves, sliding columns, pull wires, and adjusting plates; a top of the clamping sleeve is vertically welded to a bottom of the handle, a bottom of the clamping sleeve is fixed to the flexible sleeve, three groups of the sliding grooves having a depth of twelve millimeters are uniformly distributed in the clamping sleeve along a left-to-right end, each of the clamping grooves having a semicircular shape is respectively formed in a middle right end and an upper end of each of the sliding grooves, each of the sliding columns is respectively disposed in each of the sliding grooves, and each of the sliding columns is respectively and slidably connected with each of the sliding grooves; each of the pull wires is respectively embedded at a bottom of each of the sliding columns, and a bottom of each of the pull wires penetrates through a bottom of the clamping sleeve and is respectively fixed with each of the adjusting plates.

3. The flexible medical scissors according to claim 2, wherein each of the adjusting plates comprises a fixing plate, a first connecting plate, rotation shafts, wire columns, a second connecting plate, and a rotating plate; a first of the rotation shafts is embedded in a lower end in the fixing plate, and the first of the rotation shafts rotates with a first end of the first connecting plate on an outer diameter surface of the first of the rotation shafts, a first of the wire columns is vertically fixed on a top of the first of the rotation shafts, and an outer diameter surface of the first of the wire columns is fixedly wound with a respective of the pull wires, a second end of the first connecting plate is further rotated with a first end of the second connecting plate through a second of the rotation shafts, and a second end of the second connecting plate is rotated with the rotating plate through a third of the rotation shafts; a movable shaft is embedded in a lower end of the rotating plate, and the movable shaft is fixed with an upper end in the first fixing disc through a steel plate.

4. The flexible medical scissors according to claim 3, wherein three groups of the wire columns are disposed on each of the adjusting plates, and each lower end of the pull wires is respectively fixed to the three groups of the wire columns.

5. The flexible medical scissors according to claim 2, wherein bottom five centimeters portions of the pull rope and the pull wires, are all elastic, and a maximum stretching length is eight centimeters.

6. The flexible medical scissors according to claim 2, wherein an outer diameter of each of the sliding columns is smaller than an inner diameter of each of the sliding grooves and an inner diameter of each of the clamping grooves, and a lower end of the outer diameters of each of the sliding columns is frosted.

7. The flexible medical scissors according to claim 1, wherein an inner diameter of the finger sleeve is 1.2 centimeters, and an inner surface of the finger sleeve is bonded with a layer of anti-skid silica gel layer.

8. The flexible medical scissors according to claim 1, wherein an upper three centimeters end of the connecting wire is an elastic portion, and a bottom of the connecting wire is a fixed portion.

9. The flexible medical scissors according to claim 1, wherein an outer diameter of the movable ball is smaller than a top width of the annular groove.

* * * * *